United States Patent
Donelon et al.

(10) Patent No.: US 6,585,872 B2
(45) Date of Patent: Jul. 1, 2003

(54) EXHAUST GAS SENSOR

(75) Inventors: Matthew J. Donelon, Witchita Falls, TX (US); Paul Kikuchi, Fenton, MI (US); Marsha E. Nottingham, Howell, MI (US)

(73) Assignee: Delphi Technologies, Inc., Troy, MI (US)

(*) Notice: Subject to any disclaimer, the term of this patent is extended or adjusted under 35 U.S.C. 154(b) by 130 days.

(21) Appl. No.: 09/741,662

(22) Filed: Dec. 19, 2000

(65) Prior Publication Data

US 2002/0108853 A1 Aug. 15, 2002

(51) Int. Cl.$^7$ ............................................. G01N 27/407
(52) U.S. Cl. ................... 204/424; 204/427; 204/428; 204/291; 204/292; 427/125; 427/126.3; 427/419.2
(58) Field of Search ........................... 204/421–429, 204/291, 292

(56) References Cited

U.S. PATENT DOCUMENTS

| | | | |
|---|---|---|---|
| 3,941,673 A | | 3/1976 | Takao et al. |
| 4,304,652 A | * | 12/1981 | Chiba et al. |
| 4,379,741 A | * | 4/1983 | Sand et al. |
| 4,818,364 A | * | 4/1989 | Weber et al. |
| 5,139,639 A | | 8/1992 | Holleboom |
| 5,271,821 A | | 12/1993 | Ogasawara et al. |
| 5,360,528 A | | 11/1994 | Oh et al. |
| 5,384,030 A | | 1/1995 | Duce et al. |
| 5,423,972 A | | 6/1995 | Mann et al. |
| 5,762,737 A | | 6/1998 | Bloink et al. |
| 5,849,165 A | | 12/1998 | Kojima et al. |

OTHER PUBLICATIONS

U.S. patent application Ser. No. 09/739,520, Clyde et al., filed Dec. 15, 2000.

Haaland, "Noncatalytic Electrode for Solid Electrolyte Oxygen Sensors", J. of the Electrochemical Soc., Apr. 1980, vol. 107, No. 4, pp. 796–804. XP–002084798.

* cited by examiner

Primary Examiner—T. Tung
(74) Attorney, Agent, or Firm—Vicent A. Cichosz

(57) ABSTRACT

Disclosed herein is a gas sensor having a small amount of lead oxide incorporated into an inner electrode and an outer electrode, and a method for depositing the lead oxide. The lead oxide is applied in an amount sufficient to effectuate consistent performance during sensor break-in. Lead oxide is transferred to the electrodes of the sensor element during the fabrication process by exposing the sensor element to glass having a known lead content during a heating step. Lead oxide from the glass is vaporized and deposited on the electrodes in the form of lead oxide. The deposited lead oxide is incorporated into the electrodes of the sensor element. The lead oxide reduces performance irregularities thereby improving performance during the initial use of the gas sensor.

17 Claims, 6 Drawing Sheets

EXHAUST GAS SENSOR

BACKGROUND

This disclosure relates generally to exhaust gas sensors, and specifically to reduction of inconsistencies in break-in performance in exhaust oxygen sensors.

Oxygen sensors are used in a variety of applications that require qualitative and quantitative analysis of gases. For example, oxygen sensors have been used for many years in automotive vehicles to sense the presence of oxygen in exhaust gases, such as when an exhaust gas content switches from rich to lean or lean to rich. In automotive applications, the direct relationship between oxygen concentration in the exhaust gas and the air-to-fuel ratio of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically consists of an ionically conductive solid electrolyte material, a porous platinum electrode which is exposed to the exhaust gases, and a porous electrode on the sensor's interior surface exposed to a known oxygen partial pressure. Sensors typically used in automotive applications use a yttria-stabilized, zirconia-based electrochemical galvanic cell operating in potentiometric mode to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia electrolyte, according to the Nernst equation:

$$E = \left(\frac{RT}{4F}\right)\ln\left(\frac{P_{O_2}^{ref}}{P_{O_2}}\right)$$

where:
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressures between fuel rich and fuel lean exhaust conditions, the electromotive force changes sharply at the stoichiometric point, giving rise to the characteristic switching behavior of these sensors. Consequently, these potentiometric oxygen sensors indicate qualitatively whether the engine is operating fuel rich or fuel lean, without quantifying the actual air to fuel ratio of the exhaust mixture.

When first put into use, exhaust oxygen sensors exhibit a "green" effect, which produces inconsistent performance during the initial use of the sensor. Engine calibration must typically account for the green effect, which makes calibration more difficult. After several hours of use, the green effect disappears, and more reliable sensor performance is seen.

To reduce the green effect, conventional oxygen sensors incorporate various elements into the ink used to form the electrodes. Sodium, magnesium, and potassium, in particular, have been incorporated into ink prior to electrode formation in an attempt to ameliorate the green effect. This approach, however, can incorporate excessive amounts of the elements in the finished sensor element, which causes a degradation in the performance of the sensor.

What is needed in the art is a gas sensor with a reduced green effect.

SUMMARY

The above-described and other disadvantages of the prior art are overcome by the sensor element described herein. The exhaust gas sensor element comprises an electrolyte body having a first surface and a second surface. Disposed in intimate contact with the first surface is a first electrode, while a second electrode is disposed in intimate contact with the second surface. The second electrode comprises lead oxide in an amount of about 0.1 to about 8 $mg/cm^2$.

The method for making the gas sensor element comprises forming an electrolyte body and forming an electrode ink comprising a first catalyst. The electrode ink is applied to a first surface and a second surface of the electrolyte body. The body is sintered to form a catalyst layer. Lead oxide is applied to the catalyst layer in an amount of about 0.1 to about 8 $mg/cm^2$. A second catalyst is also applied to said catalyst layer, and the layer is sintering to form a first electrode and a second electrode.

The method for depositing lead oxide on a gas sensor element, comprises applying a lead oxide containing glass to a substrate. The gas sensor element is placed in a closed container with the substrate and the element is heated causing lead oxide to be liberated from the substrate in vapor form and adsorbed by the gas sensor element. The resulting sensor has a first electrode and a second electrode comprising lead oxide in an amount of about 0.1 to about 8 $mg/cm^2$.

Finally, the gas sensor comprises a middle shell, with a lower shell and an upper shell disposed in contact with the middle shell. The sensor element is disposed in contact with the middle shell, protruding into the lower shell and the upper shell. At least one electrical connector disposed in contact with a first electrode and a second electrode of the sensor element, such that electrical access is provided to the sensor element from an external circuit.

BRIEF DESCRIPTION OF THE DRAWINGS

The apparatus and method will now be described by way of example, with reference to the accompanying drawings, which are meant to be exemplary, not limiting.

DESCRIPTION OF THE PREFERRED EMBODIMENTS

A gas sensor and method of making the same is described herein, wherein lead oxide is deposited on the sensor element prior to final assembly into the gas sensor. The sensor element comprises an electrolyte body with an inner electrode disposed on the inner surface, and an outer electrode disposed on the outer surface, and a protective layer disposed over the outer electrode. Lead oxide is incorporated onto the electrolyte body underneath the electrodes through a vapor deposition process in order to improve initial performance of the gas sensor. The lead oxide incorporation process and resulting sensor element can be used in any gas sensor, with use in fast light-off, heated and unheated, gas sensors preferred. It is hereby understood that although the apparatus and method are described in relation to making an oxygen sensor, the sensor could be a nitrous oxide sensor, hydrogen sensor, hydrocarbon sensor, or the like.

Figure 1:
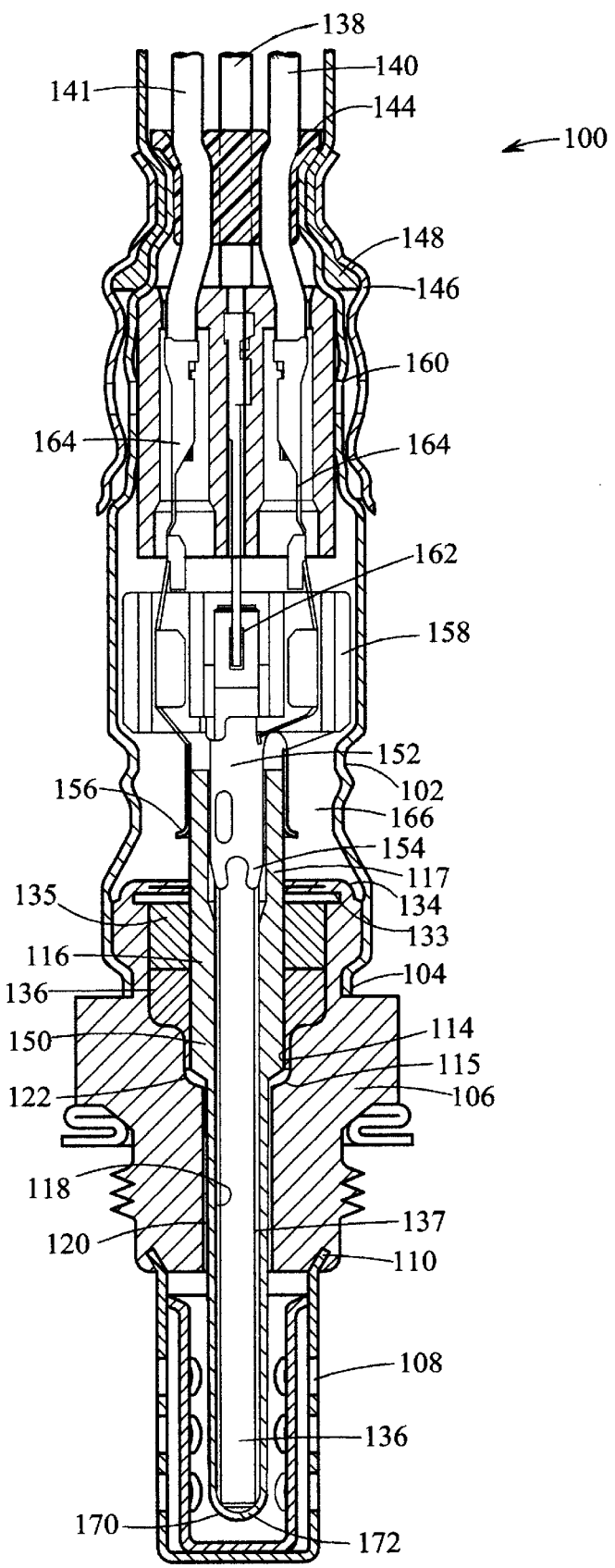
FIG. 1 is a partial cross-section of one embodiment of a gas sensor.

FIG. 1 shows a cross section of one embodiment of the automotive exhaust gas sensor generally at 100. The gas sensor includes an upper shell 102 having a lower end 104 laser welded and/or crimped to a thicker, middle shell 106. A louvered, tubular, lower shell 108 is provided, having an upper end 110 welded and/or crimped to the middle shell 106. The middle shell 106 includes a lower annular shoulder 115. A sensor element 117 is disposed through in the middle shell. The sensor element 117 can include a conical-shaped electrolyte body 116 having inner and outer electrodes 118, 120 formed thereon. The electrolyte body 116 has a lower, sloped, annular shoulder 122 which is sufficient to engage the sloped shoulder 115, with a lower gasket 114 preferably positioned between shoulders 122 and 115.

The middle shell 106 can include an annular ring 134, crimped over an upper slanted shoulder 133 of an insulator 135. The insulator 135 is disposed between the ring 134 and an optional area of compacted talc powder 136, which contacts an upper, sloped, annular shoulder 150 of the sensor element 117. The crimped annular ring 134 applies a force through the insulator 135 and talc powder 136 to hold the sensor element 117 in place, applying pressure to the annular lower gasket 114. A heating element 132 extends into a cavity 137 of the conical-shaped electrolyte body 116.

The sensor element 117 and the heating element 132 are electrically connected to external circuits through clips. An internal electrode clip 152 is preferably formed so as to fit tightly in the cavity 137 of the sensor element 117. The internal electrode clip 152 which applies an outward spring force, to ensure positive electrical contact with the inner electrode 118, comprises prongs 154 which are angled inward toward the heating element 132 in order to secure the heating element 132 centrally in place in the cavity 137.

An external electrode clip 156 can be formed so as to fit tightly around the exterior surface of the sensor element 117. By applying an inward spring force on the sensor element 117, the external electrode chip 156 ensures a positive electrical contact with the outer electrode 120. The internal electrode clip 152 and the external electrode clip 156 are disposed in a insulating clip securing block 158, which holds the internal electrode clip 152 and the external electrode clip 156 in secure relative position.

A connector assembly 160 holds heater connection clips 162 securely in place. The connector assembly 160 also comprises connectors 164, securely engaged with the internal and external electrode clips 152, 156, to provide an electrical path from an outside circuit to the heater connection clips 162 and the internal and external electrode clips 152, 156.

Four separate wires 138, 140, 141 (one not shown) are provided through a polymeric seal 144 in the upper shell 102 to make connections to the healing element 13Z and the inner electrode 118 and outer electrode 120 of the sensor element 117. The polymer seal 144 is sufficient to provide a water tight oxygen reference chamber 166 within the upper shell 102. An elastomeric wire boot 148 is disposed between the upper shell 102 and an outer shell 146, which is crimped and/or welded onto the upper shell 102 to secure the boot 148 and form a seal. The upper shell 102 is securely fastened and sealed to the middle shell 106 and the polymeric seal 144 to form an inner air reference chamber 166. The reference chamber 166 extends into the cavity 137 of the sensor element 117, between the heating element 136 and the inner electrode 118. The heating element 132 is held centrally in the cavity 137 by the inner electrode clip 152 and a complementary fit between the heating element tip 170 and the cavity terminus 17.

Figure 2:
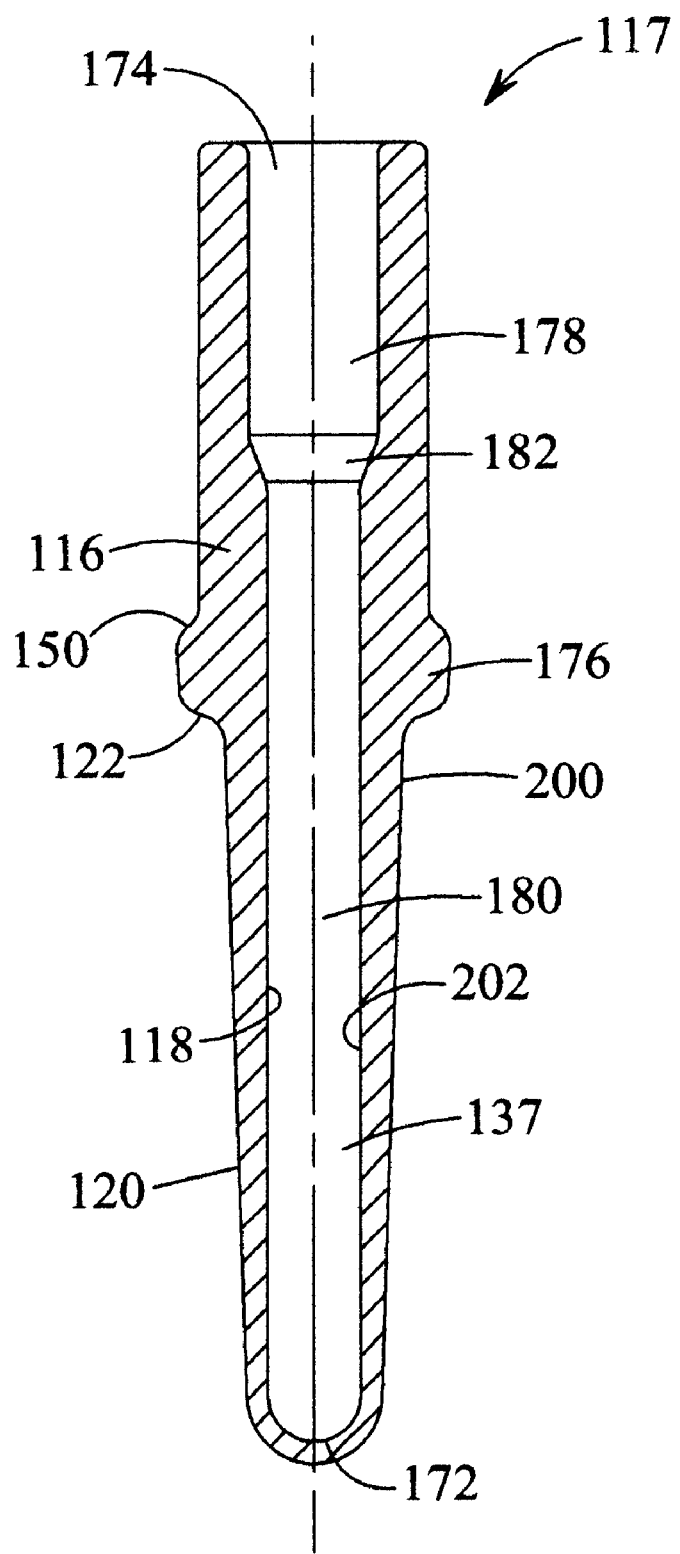
FIG. 2 is a cross-section of the sensor element of FIG. 1.

FIG. 2 is a cross-section of the sensor element 117. The electrolyte body 116 has an inner surface 202 and an outer surface 200. The sensor element 117 can be formed in any generally cylindrical shape, with a generally tapered shape from the cavity opening 174 to the cavity terminus 172 preferred. A protrusion 176 defines the upper shoulder 150 and the lower shoulder 122. The cavity 137 itself can be defined in any generally cylindrical shape. Preferably, a cylindrical top portion 178 is joined to a smaller cylindrical bottom portion 180 with a tapered portion 182. The larger cylindrical top portion 178 allows for the proper locating of the interior electrode clip 152, while the smaller cylindrical bottom portion 180 allows for a minimal gap between the heating element 132 and the inner electrode 118.

Figure 3:
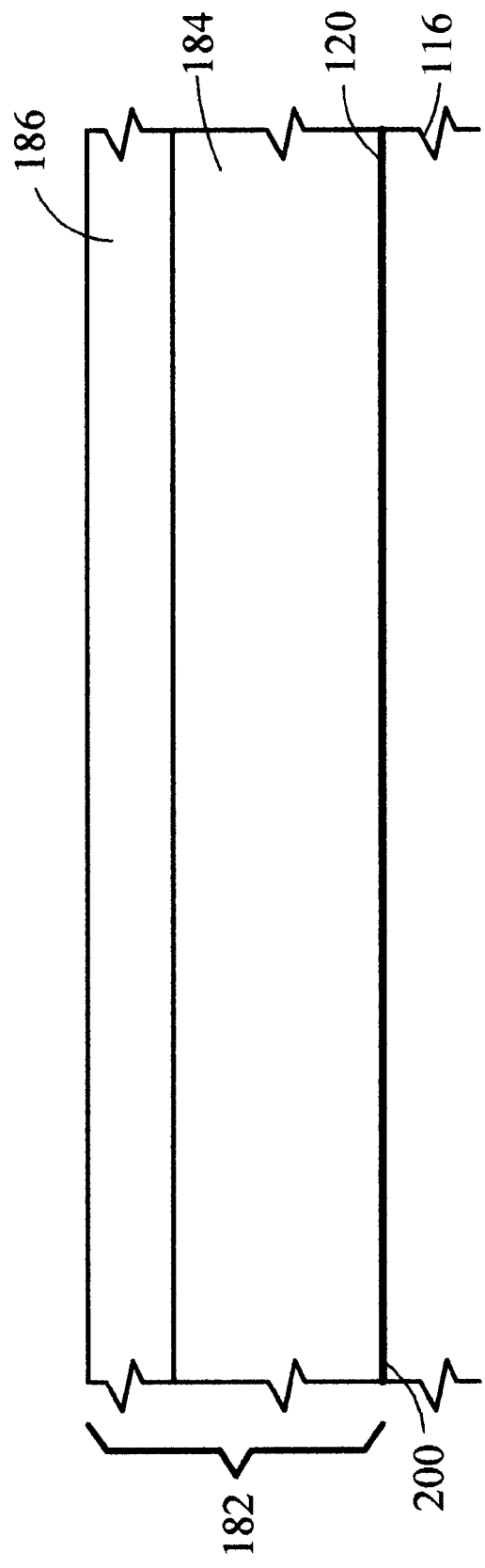
FIG. 3 is an enlarged cross section of the outer surface of the sensor element of FIG. 2.

FIG. 3 is a magnified cross-section of the outer surface of the sensor element 117 below the protrusion 176. The outer electrode is disposed between the electrolyte body 116 and a protective layer 188 which can comprise a porous material 184 and a high surface area material 186.

The method of manufacture of the gas sensor and the preferred materials for use in the gas sensor will now be discussed.

Fabrication of the sensor element 117 begins with mixing and preparation of the electrolyte body 116. The electrolyte body 116 can be any material that is capable of permitting the electrochemical transfer of oxygen ions while inhibiting the physical passage of exhaust gases, that preferably has an ionic/total conductivity ratio of approximately unity, and that is compatible with the environment in which the sensor will be utilized. Metal oxides such as zirconia, and the like, which may optionally be stabilized with calcium, barium, yttrium, magnesium, alumninum, lanthanum, cesium, gadolinium, and the like, and oxides thereof, as well as combinations comprising at least one of the foregoing electrolyte materials. For example, the electrolyte can be alumina and yttrium stabilized zirconia Typically, the solid electrolyte has a thickness of up to about 500 microns, with a thickness of approximately 25 microns to about 500 microns preferred, and a thickness of about 50 microns to about 200 microns especially preferred. Other additives, such as wax, organic powders, and the like can be added to improve the perform a ace characteristics of the sensor element 117.

The electrolyte body 116 can be formed by any conventional technique. For example, the desired electrolyte materials in the form of near submicron powders and granulated additives can be combined to form a mixture which is compacted in a mold at pressures sufficient to achieve the desired density. The applied pressure is typically greater than about 8 ksi (kilopounds per square inch), with greater than about 10 ksi preferred. The mold, which can be a conventional mold, such as a urethane mold, produces an oversized electrolyte blank in order to allow for shrinkage in later steps. The electrolyte blank is ground to the desired shape using conventional grinding techniques, such as employing an appropriately contoured grinding wheel. The ground electrolyte body is then optionally sintered at high temperatures to impart strength. Sintering is carried out for a time and at a temperature sufficient to appropriately strengthen the part, e.g. at about 1,000° C. to about 1,200° C. for up to about 2 hours or so, with about 1,050° C. to about 1,150° C. for about 1 to about 2 hours preferred.

The inner and outer electrodes 118, 120, which are disposed in contact with the inner surface 202 and outer surface 200 of the electrolyte body 116, can comprise any catalyst capable of ionizing oxygen, including, but not limited to, metals such as platinum, palladium, gold, osmium, rhodium, iridium, ruthenium, zirconium, yttrium, cerium, calcium, aluminum, and the like, as well as alloys, oxides, and combinations comprising at least one of the foregoing metals. The catalyst is combined with a vehicle, such as an organic vehicle, to form an electrode ink. The application of the outer electrode 120 is accomplished by the application of the electrode ink to the outer surface 200 of the electrolyte body 116 using conventional techniques, such as spraying, painting, dipping, physisorbing, imbibing, pad printing, and the like, and allowing the vehicle to adsorb into the electrolyte body 116. Formation of the inner electrode 118 comprises filling the cavity 137 with the electrode ink, removing the excess electrode ink, and allowing the vehicle of the remaining electrode ink to absorb into the electrolyte body 116. After vehicle adsorption, precursor catalytic electrode layers are present on both the outer surface 200 and the inner surface 202 of the electrolyte body 116.

The electrolyte body 116, with electrode layers 118, 120, is then subjected to a high temperature sintering step to preferably fully densify the part. The second sintering is performed at about 1,300° C. to about 1,700° C., with a temperature of about 1,400° C. to about 1,600° C. preferred. Sintering is performed for a sufficient period of time to preferably fully densify the part, e.g., typically greater than about 1 hour.

At this point, the outer and inner electrodes 118, 120 are partially formed. Next, lead oxide is added to the electrode. To precisely control the lead oxide deposition for the gas sensor described above, a vapor transfer technique is used. Lead oxide (PbO) can initially be impregnated into a substrate in an amount of at least about 40 weight percent (wt %) PbO, with about 40 wt % to about 80 wt % PbO preferred, and about 60 wt % to about 80 wt % PbO especially preferred.

Any conventional ceramic or other material that can both withstand the required temperatures and serve as a substrate for the glass can be used as the substrate. For example, a conventional ceramic sagger, a crucible containing a quantity of glass, or a parts tray. A coating of ink, which comprises a lead borosilicate glass and a vehicle, such as an organic vehicle (e.g., terpineol, or the like), is applied to the substrate. In one embodiment, the ink has a composition of 60 wt % lead oxide (PbO), 20 wt % silicon dioxide ($SiO_2$), 10 wt % boron oxide ($B_2O_3$), and 10 wt % other oxides. The ink can be applied to the substrate in any conventional fashion such as spraying, dipping, and the like, with brushing the ink onto the substrate preferred.

The electrolyte body 116 with the partially formed electrodes can now be loaded onto the lead oxide coated substrate and heated in a closed environment to a temperature sufficient to vaporize the desired amount of lead oxide from the substrate. Temperatures of about 800° C. to about 1,200° C. can typically be used, with about 900° C. to about 1,100° C. preferred, and about 975° C. to about 1,050° C. especially preferred, for about 0.5 hours to about 5 hours, with about 1 hour to about 3 hours preferred. The vaporized lead oxide is adsorbed by the outer surface of the electrolyte body 116 with the partially formed electrodes, thereby incorporating lead oxide into the partially formed electrodes at a controlled rate to form a precursor. Tile final concentration of adsorbed lead oxide on the exposed surfaces of the electrodes is about 0.10 to about 8 $mg/cm^2$ (micrograms per square centimeter), with about 1 to about 6 $mg/cm^2$ preferred, about 2 to about 4 $mg/cm^2$ more preferred, and about 2.2 to about 2.5 $mg/cm^2$ especially preferred. The lead coated precursor is then cooled to room temperature (i.e., by forced-air cooling).

Next, the precursor can be coated on the outside surface with more catalyst. The catalyst can be applied with conventional techniques, with a sputtering process preferred. The catalyst is preferably applied to a thickness of about 1 to about 50 angstroms, with a thickness of about 3 to about 10 angstroms preferred. The precursor is then sintered for a third time at a temperature sufficient to securely adhere the catalytic coating. The third sintering is typically performed at about 500° C. to about 1,000° C., with a temperature of about 700° C. to about 900° C. preferred.

The electrodes 118, 120 are now complete, and a protective porous material 184 can be applied to the exterior surface of the precursor. Any porous material that allows passage of exhaust gases while preventing passage of unwanted contaminants can be used, such as magnesium aluminate, aluminum oxide, and combinations comprising at least one of the foregoing, among others. The porous material 184 is typically applied to a thickness of about 50 to about 200 microns, with a thickness of about 90 to about 140 microns preferred.

To further protect the sensor element 117, a high surface area material 186 which can trap poisons in the exhaust can optionally be applied to the exterior surface of the sensor element, preferably to the portion of the sensor element 117 between the protrusion 176 and the terminus 17 on the exterior surface. The high surface area material 186 can be any material that has a porosity sufficient to allow the passage of exhaust gases, such as aluminum oxide, and other metal oxides. The high surface area material 186 preferably has a surface area of greater than about 150 meters squared per gram ($m^2/g$), with a surface area of greater than about 200 ($m^2/g$) preferred. The high surface area material 186 is then dried, and the sensor element 117 is sintered at a temperature sufficient to harden the high surface area material 186, e.g., a temperature of about 400° C. to about 600° C., with a temperature of about 450° C. to about 550° C. preferred.

Manufacture of the sensor element 117 can optionally be completed with a heat treatment in a pure nitrogen atmosphere for at a temperature sufficient to remove any unwanted oxide film from the catalyst material. For example for a period of about 0.5 to about 1 hour at a temperature of about 600° C. to about 1,000° C., with about 700° C. to about 900° C. preferred.

The completed sensor element is then incorporated into the gas sensor through conventional means.

Figure 4:
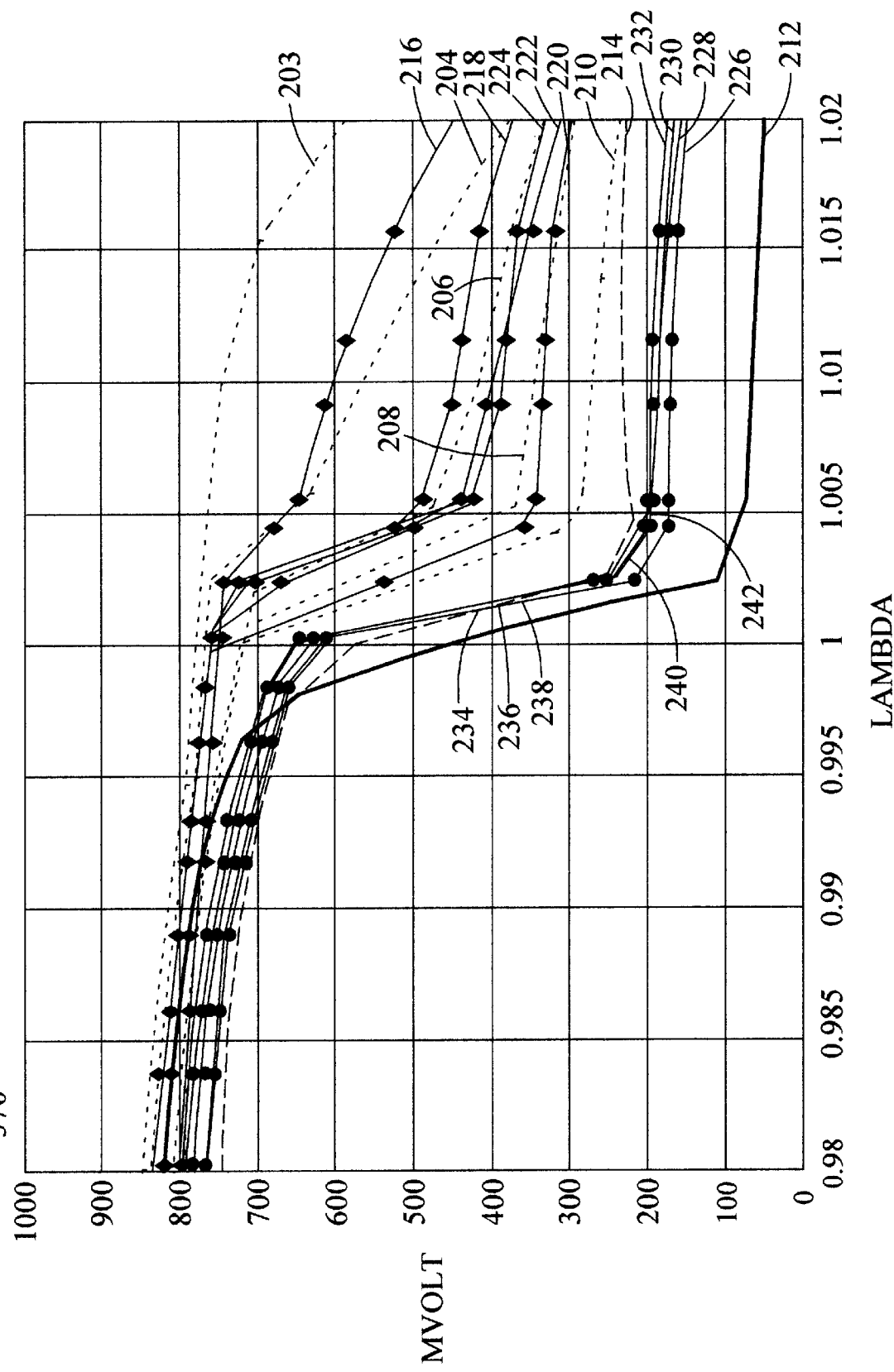
FIG. 4 is a plot showing the relative performance of gas sensors treated with lead oxide and gas sensors without lead oxide.

FIG. 4 is a plot showing the performance of several exemplary sensors incorporating lead oxide in the defined amounts and sensors not incorporating lead oxide. In FIG. 4, lines 203, 204, 206, 208, and 210 represent the performance of sensors lacking lead oxide in the electrodes 118, 120. Line 212 is an aged sensor reference, and line 214 is a de-greened sensor. Lines 216, 218, 220, 222, and 224 represent the performance of sensors incorporating lead oxide at a temperature of 600° C. Lines 226, 228, 230, and 232 represent the performance of sensors incorporating lead oxide at a temperature of 700° C. Lines 234, 236, 238, 240, and 242 represent the performance of sensors incorporating lead oxide at an operating temperature of 800° C.

Figure 5:
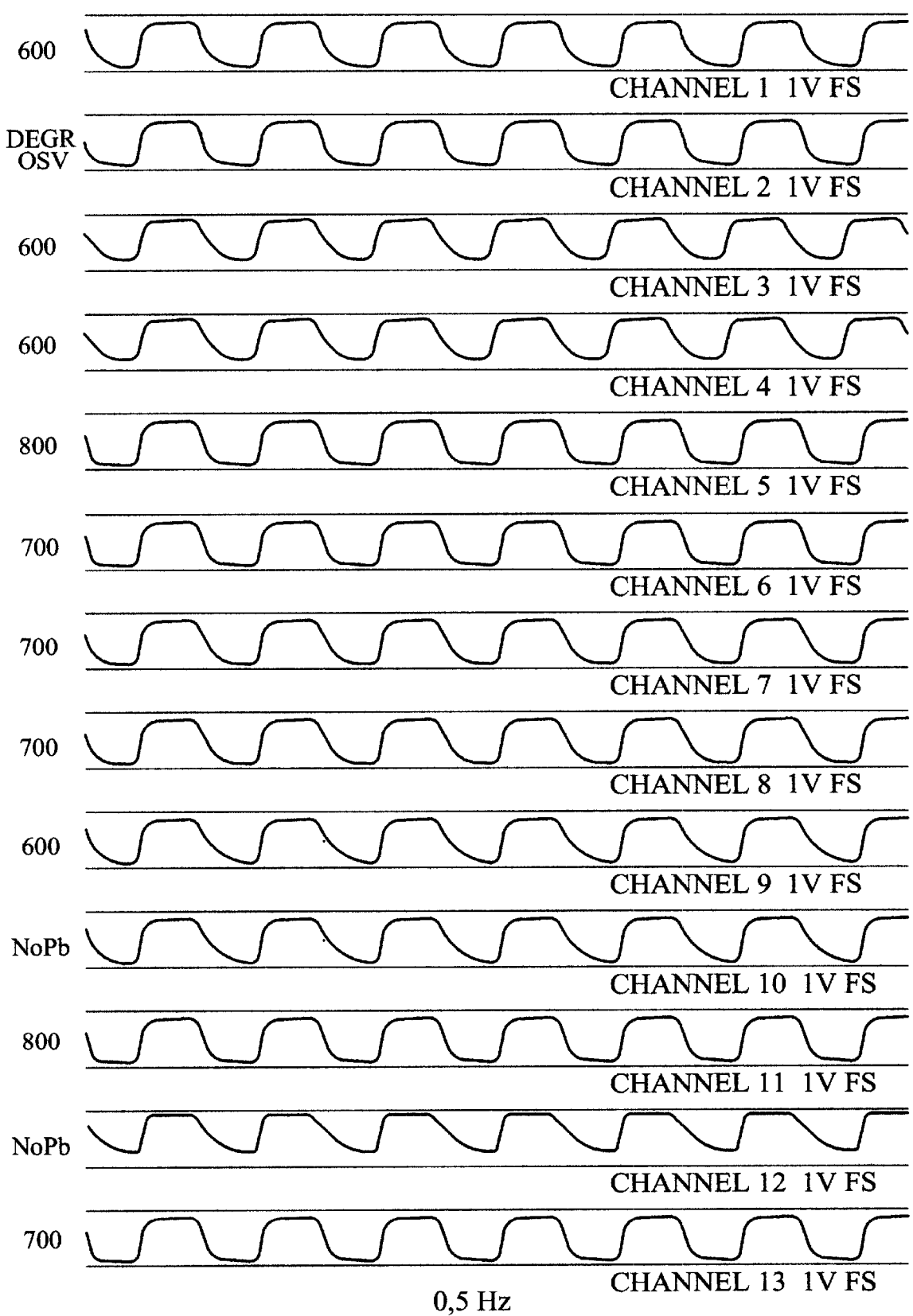
FIG. 5 shows several dynamic plots of various sensors with and without lead oxide.
Figure 6:
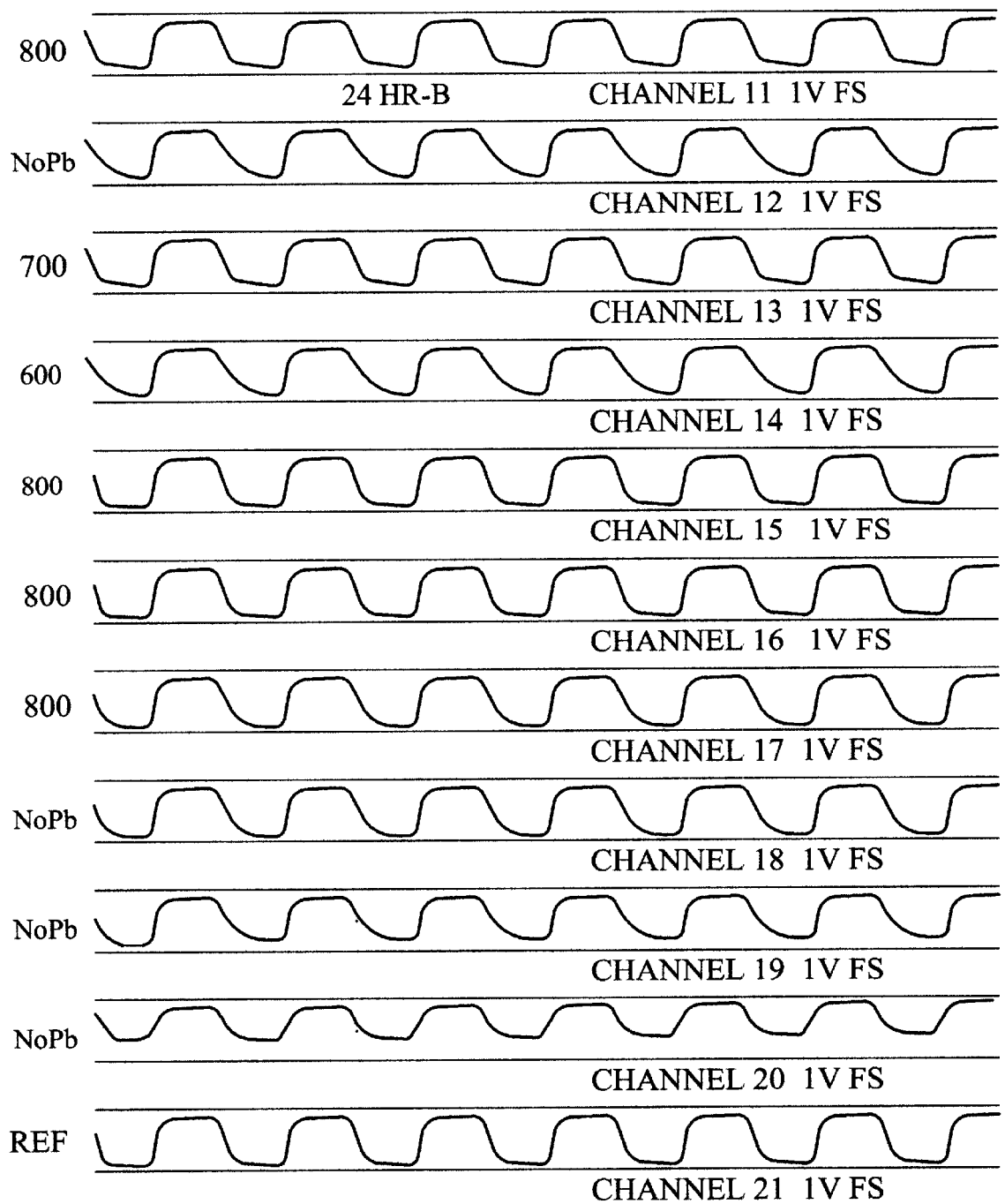
FIG. 6 shows several dynamic plots of various sensors with and without lead oxide.

FIGS. 5 and 6 represent the voltage outputs against time for oxygen sensors. The elements were tested at temperatures of 600° C., 700° C., and 800° C. The sensing elements were tested for 24 hours prior to collection of sampling data. A sample of a de-greened oxygen sensor is also illustrated with about 8.72 to about 15 $mg/cm^2$ of lead thereon. Following testing, the amount of lead detectable for each treatment temperature was; at 600° C. lead was not detected, at 700° C. lead was detected at 0.59 $mg/cm^2$, and at 800° C. lead was detected at 2.25 $mg/cm^2$. The curves indicate the variability of the pitch of the curve when the sensor switches from rich to lean conditions. The vertical pitch of the curve indicates a quick response time while the more horizontal pitch demonstrates a long response time. The Figures illustrate that at temperatures of 800° C. the elements closely mimic the results for a de-greened part.

The gas sensor described above incorporates lead oxide into the electrodes 118, 120, thereby improving sensor performance during initial use of the sensor by reducing the time required to desorb carbon monoxide. While other oxygen sensors also have a light-off temperature of 370° C., they do not perform as well as this sensor. The sensor performs well at low temperatures (i.e., at startup) and helps to achieve greater control over the sensor performance. When there is a sufficient amount of lead, there is a drastic reduction in part to part variability when switching from fuel rich to fuel lean. Another advantage is that this sensor makes it easier to calibrate engines, as well as making parts more repeatable.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

What is claimed is:

1. An exhaust gas sensor element, comprising:
   an electrolyte body having a first surface and a second surface;
   a first electrode in intimate contact with said first surface; and,
   a second electrode in intimate contact with said second surface, said second electrode comprising lead oxide in an amount of about 0.1 to about 8 $mg/cm^2$.

2. The element of claim 1, further comprising a protective layer in intimate contact with said second electrode.

3. The element of claim 1, wherein said first electrode and said second electrode comprise lead oxide in an amount of about 1 to about 6 $mg/cm^2$.

4. The element of claim 3, wherein said first electrode and said second electrode comprise lead oxide in an amount of about 2 to about 4 $mg/cm^2$.

5. The element of claim 4, wherein said first electrode and said second electrode comprise lead oxide in an amount of about 2.2 to about 2.5 $mg/cm^2$.

6. The element of claim 1, wherein said second electrode further comprises a catalyst capable of ionizing oxygen.

7. The element of claim 1, wherein the second electrode further comprises a catalyst.

8. A gas sensor comprising:
   a middle shell;
   a lower shell disposed in contact with said middle shell;
   an upper shell disposed in contact with said middle shell opposite said lower shell;
   a sensor element disposed in contact with said middle shell, and protruding into said lower shell and said upper shell, said sensor element comprising:
   an electrolyte body having a first surface and a second surface;
   a first electrode disposed on said first surface;
   a second electrode disposed on said second surface, said second electrode comprising lead oxide in an amount of about 0.1 to about 8 $mg/cm^2$; and,
   a protective layer disposed on said second electrode; and,
   at least one electrical connector disposed in contact with said first electrode and said second electrode, wherein said at least one electrical connector provides electrical access to said sensor element from an external circuit.

9. The gas sensor of claim 8, wherein said first electrode and said second electrode comprise lead oxide in an amount of about 1 to about 6 $mg/cm^2$.

10. The gas sensor of claim 9, wherein said first electrode and said second electrode comprise lead oxide in an amount of about 2 to about 4 $mg/cm^2$.

11. The gas sensor of claim 10, wherein first electrode and said second electrode comprise lead oxide in an amount of about 2.2 to about 2.5 $mg/cm^2$.

12. The gas sensor of claim 8, wherein said second electrode further comprises a catalyst capable of ionizing oxygen.

13. A gas sensor element, comprising:
    an electrolyte body having a first surface and a second surface;
    a first electrode in intimate contact with said first surface;
    a precursor comprising lead oxide adsorbed on a exposed surface of a second electrode, wherein said second electrode is in intimate contact with said second surface; and
    a catalyst coated on said precursor.

14. The gas sensor element of claim 13, wherein said lead oxide is present in an amount of about 0.1 to about 8 $mg/cm^2$.

15. The gas sensor element of claim 1, further comprising a catalyst disposed on said lead oxide.

16. The gas sensor element of claim 15, wherein said catalyst has a thickness of about 1 to 50 angstroms.

17. The gas sensor element of claim 15, further comprising a protective layer disposed on said catalyst, wherein said protective layer has a thickness of about 50 to about 200 microns and is selected from the group consisting of magnesium aluminate, aluminum oxide, and combinations comprising at least one of the foregoing.

* * * * *